United States Patent [19]

Panzone et al.

[11] Patent Number: 4,994,555
[45] Date of Patent: Feb. 19, 1991

[54] PROCESS FOR RECOVERY OF GLYCOPEPTIDIC ANTIBIOTICS

[75] Inventors: Giambattista Panzone, Cornaredo; Anacleto Gianantonio, Milan, both of Italy

[73] Assignee: Gruppo Lepetit S.p.A., Milan, Italy

[21] Appl. No.: 528,274

[22] Filed: May 21, 1990

Related U.S. Application Data

[63] Continuation of Ser. No. 253,936, Oct. 5, 1988, abandoned, which is a continuation of Ser. No. 36,211, Apr. 9, 1987, abandoned.

[30] Foreign Application Priority Data

Apr. 11, 1986 [GB] United Kingdom ............... 8608798

[51] Int. Cl.$^5$ .............................................. C07K 1/14
[52] U.S. Cl. .................................... 530/344; 530/317; 530/322; 435/71.3
[58] Field of Search ..................... 530/317, 322, 344; 435/71.3

[56] References Cited

U.S. PATENT DOCUMENTS

| | | | |
|---|---|---|---|
| Re. 32,333 | 1/1987 | Hamill et al. | 530/321 |
| 3,531,463 | 9/1970 | Gustafson | 536/25 |
| 4,064,233 | 12/1977 | Hammill et al. | 424/118 |
| 4,122,168 | 10/1978 | Michel et al. | 424/118 |
| 4,239,751 | 12/1980 | Coronelli et al. | 424/118 |
| 4,322,406 | 3/1982 | Debono et al. | 424/118 |
| 4,440,753 | 4/1984 | McCormick | 424/124 |
| 4,462,942 | 7/1984 | Hamill et al. | 530/317 |
| 4,667,024 | 5/1987 | Stirin et al. | 536/16.9 |
| 4,935,238 | 6/1990 | Selva et al. | 424/118 |

FOREIGN PATENT DOCUMENTS 122969 10/1984 European Pat. Off. .
813559 5/1959 United Kingdom .

Primary Examiner—Johnnie R. Brown
Assistant Examiner—Christina Chan
Attorney, Agent, or Firm—J. Michael Dixon

[57] ABSTRACT

This invention concerns the recovery of glycopeptidic antibiotics from aqueous solutions resulting from fermentation broths or process streams. Examples of glycopeptidicantibiotics to which the process of this invention may be applied are the following: vancomycin, actaplanin, ristocetin, avoparcin, actinoidin, LL-AM-374, A 477, OA 7653, A 35512 B, A 515668, AAD 216, A 41030, A 47934, A-40926 (European Pat. Appln. No. 85112406.5), the individual factors, derivatives and pseudo-aglycones and aglycones thereof, teicoplanin and teicoplanin-like compounds.

11 Claims, No Drawings

PROCESS FOR RECOVERY OF GLYCOPEPTIDIC ANTIBIOTICS

CROSS-REFERENCE TO RELATED APPLICATION

This is a continuation of application Ser. No. 253,936, filed Oct. 5, 1988, now abandoned, which is a continuation of application Ser. No. 036,211, filed Apr. 9, 1987, now abandoned.

This invention concerns the recovery of glycopeptidic antibiotics from aqueous solutions resulting from fermentation broths or process streams. Examples of glycopeptidicantibiotics to which the process of this invention may be applied are the following: vancomycin, actaplanin, ristocetin, avoparcin, actinoidin, LL-AM-374, A 477, OA 7653, A 35512 B, A 515668, AAD 216, A 41030, A 47934, A-40926 (European Pat. Appln. No. 85112406.5), the individual factors, derivatives and pseudo-aglycones and aglycones thereof, teicoplanin and teicoplanin-like compounds.

Separation of biologically active materials, including antibiotics, from aqueous media by absorption on a solid matrix is described in U.S. Pat. No. 3,531,463. In said case non-ionogenic, macroreticular, water insoluble polyvinylbenzene resins are employed.

Recovery of ristocetin from the filtered fermentation broth by adsorption on cation-exchange resins containing acidic groups is described in U.K. Patent No. 813559. Recovery and purification of vancomycin and actaplanin antibiotics by adsorption on macroporous non functional styrene-divinylbenzene copolymer resins is described in U.S. Pat. No. 4,440,753.

Separation of single factors of antibiotic A-4696 (actaplanin) from a purified preparation of A-4696 complex by means of column chromatography on a polyamide column is described in U.S. Pat. No. 4322406.

The preparation of crystalline A-4696 from crude A-4696 hydrochloride isolated from the fermentation broth is described in U.S. Pat. No. 4,064,233. In this case, the isolation of crude A-4696 complex from fermentation broth include several troublesome operations such as absorption on a carbon column, elution, elimination of sulfate ions, concentration, dissolution in water, further absorption on activated carbon, further elution with an hydrochloric acid/acetone solution, concentration of the eluate and precipitation of crude A-4696 hydrochloride by addition of methanol.

The isolated crude A-4696 hydrochloride is then dissolved in water and the solution is passed over a polyamide resin column which is then washed with a water stream. The antibiotic activity is then recovered from the effluent by evaporation and further dissolved in water/methanol, acidified with HCl and precipitated by addition of acetone to yield the purified hydrochloride of A-4696 which is then re-crystallized from water/ethanol.

The separation of single factors of antibiotic A-35512 from a sample of the isolated complex by high performance liquid chromatography using a polyamide resin as stationary phase is described in U.S. Pat. No. 4,122,168. In this case, the previous separation of the complex from the fermentation broth is carried out by absorption on a macroporous non-ionic polystyrene resin (Amberlite XAD-4).

Examples of recovery and purification of glycopeptidic antibiotics by means of affinity chromatography on immobilized ligand containing a D-alanyl-D-alanine oligopeptides are described in European Patent Applications Publications No. 122969 and No. 132117, respectively.

According to this invention it has been discovered that glycopeptidic antibiotics can be suitably isolated from aqueous solutions which contain said substances accompanied by considerable amounts of several undesired products of different kind and origin by absorption on certain polyamide chromatography resins followed by elution with aqueous mixtures.

The object of this invention is, in fact, a process for recovering glycopeptidic antibiotics from aqueous solutions resulting from fermentation broths or process streams which comprises contacting said aqueous solution with a polyamide chromatography resin capable of absorbing said antibiotic activity, separating the resin from the aqueous solution, washing the resin with an aqueous mixture eluent and recovering the glycopeptidic antibiotic from said eluent.

Typical aqueous solutions containing glycopeptidic antibiotics accompanied by undesired products are fermentation broths filtered from the mycelia or partially purified process streams.

Examples of the undesired accompanying products mentioned above are for instance colored impurities, side-products, unexhausted reactants of the manufacture process, as well as salts and water soluble components of the fermentation media.

None of the cases referred above describes isolation of glycopeptidic antibiotic substances from aqueous solutions resulting from fermentation broths or process streams by means of absorption on a polyamide matrix. The above cited literature teaches only that chromatography on a polyamide matrix can be used for separating a glycopeptidic antibiotic complex into its single components after it has been isolated from the fermentation broth by other means. All specific examples of isolation of glycopeptidic antibiotics from the fermentation broth by means of absorption on a solid matrix referred to in the literature mentioned above regard the use of ion exchange resins or macroporous non-ionic polystyrene resins.

According to a particular aspect of this invention, the use of polyamide resins finds suitable applications in the recovery and purification steps of the manufacture process of teicoplanin and teicoplanin-like compounds. Teicoplanin is a glycopeptidic antibiotic complex produced by *Actinoplanes teichomyceticus* nov. Sp. ATCC 31121 and active against anaerobic gram-positive bacteria. As employed in its biological application teicoplanin essentially consists of factor $A_2$ (T-A2) accompanied by minor amount of factor $A_3$ (T-A3). Factor $A_2$ which in the usual chromatographic systems (e.g. thin layer chromatography and paper chromatography) behaves as a homogeneous product, when examined by reverse phase high performance chromatography shows five major components of very similar polarity designated as TA2-1, TA2-2, TA2-3, TA2-4, and TA2-5. See for instance A. Borghi et al., in the Journal of Antibiotics, Vol. 37, No. 6, pp. 615–620, June 1984. Teicoplanin and its major components are characterized by the presence of both a primary amino and a carboxylic function.

With the term "teicoplanin" as used here it is intended the product as described above. With the term "teicoplanin-like compounds" are intended each of the single factors T-$A_2$ and T-$A_3$, and each of the five major components of T-A$_2$ as well as the mixtures thereof in any proportions, such as, for instance, those obtainable by adding appropriate precursors to the fermentation media according to U.K. Patent Application No. 8512795. The term "teicoplanin-like compounds" includes also teicoplanin aglycone and pseudo-aglycones identified in the prior literature as antibiotics L 17046 (European Patent Application Publication No. 119574), L 17054 (European Patent Application Publication No. 119575) and L 17392 (European Patent Application Publication No. 146053) as well as the semi-synthetic derivatives such as esters and amides of teicoplanin and its aglycone and pseudo-aglycones (e.g. see Int. Appln. PCT/EP85/00262, U.K. Pat. Appln. Ser. No. 8522574, European Patent Applications No. 85113810.7 and No. 86112226.5). Isolation of teicoplanin from the filtered fermentation broth of *Actinoplanes teichomyceticus* nov. sp. ATCC 31121 as described in the prior literature (M.R. Bardone et al., Journal of Antibiotics, Vol. 31, No. 3, pp 170–177, March 1978) involves extraction with butanol at acidic pH followed by washing and concentration operations. This procedure, as well as any alternative use of strongly acidic ion exchange resins, provokes some degradation of the sugar moiety. The use of strongly basic ion exchange resins, on the contrary, favors epimerization which leads to loss of biological activity. Moreover, the poor specificity of the ionic resins does not favor the separation of the glycopeptidic antibiotics from all the colored impurities and side-products contained in the aqueous solutions. Non ionic macroporous resins (as well as ion exchange resins) have the disadvantage of almost irreversibly binding considerable amounts of antibiotic substance and therefore its elution require conditions which are not compatible with the chemical stability of the product. Use of affinity chromatography on immobilized ligands containing D-alanyl-D-alanine oligopeptides, although effective, has serious economic drawbacks for industrial scale operations.

Polyamide resins that have been found useful in the processes of separation of glycopeptidic antibiotics from aqueous solutions and, in particular, of teicoplanin, teicoplanin-like compounds, and antibiotic A 40926 are selected from the polyamide column chromatography resins generally identified as polycaprolactame, nylons (6/6, 6/9, 6/10 and 6/12) and the cross-linked polyvinylpyrrolidone. Said chromatography polyamide resins are generally characterized by a pore volume(*) (ml/g) ranging between 1 and 5, surface area(*) (m$^2$/g) ranging between 1 and 100, apparent density (g/ml) ranging between 0.15 and 0.50, average pore diameter(*) (Ångstrom units) ranging between 100 and 3000 and particles size distribution where at least 40 percent of the particles have size lower than 300 μ.

Specific examples of commercially available polyamide column chromatography resins suitable for the embodiment of this invention are the following: the polyamide resins Polyamide-CC 6, Polyamide-SC 6, Polyamide-CC 6.6, Polyamide-CC 6AC and Polyamide-SC 6AC of Macherey-Nagel & Co. (West Germany), the polyvinylpyrrolidone resin PVP-CL of Aldrich Chemie GmbH & Co, KG (West Germany), the polyamide resin PA 400 of M. Woelm (West Germany). For example, two of the resins indicated above have the following characteristics:

| Resin | pore volume(*) (ml/g) | surface area(*) (m$^2$/g) | apparent density (g/ml) | Average pore diameter(*) (Å) | particle size distribution |
|---|---|---|---|---|---|
| Polyamide SC 6 | 3.4 | 16.5 | 0.25 | 2000 | 60% <350μ |
| PA 400 | 2.8 | 21.5 | 0.28 | 1000 | 100% <300μ |

(*)measured with a mercury porosimeter model Serie 200 of C. Erba SpA, Milano, Italy According to a general procedure for the embodiment of this invention, an aqueous solution resulting from the fermentation broth of a glycopeptidic antibiotic filtered from mycelial cake or a process stream derived from said broth or from a chemical modification reaction on a glycopeptidic antibiotic (in particular, teicoplanin, a teicoplanin-like compound or antibiotic A 40926) is applied to a polyamide resin column at a flow rate of the fluid through the column which may range from about 20 ml/cm$^2$ per hour to about 400 ml/cm$^2$ per hour. When high flow rate is required, the aqueous solution is applied to the column under vacuum with suction from the bottom or under pressure or using a polyamide resin having larger particle size. In the latter case a slight decrease in the adsorption capacity of the resin is observed.

Alternatively, the polyamide resin can be added to the aqueous solution containing the antibiotic activity and mixed thoroughly for a determined period of time which may vary from one half hour to six hours, and then the exhausted solution is removed.

The fermentation broth or the process stream from which the aqueous solution containing the antibiotic activity is obtained are produced according to the standard pilot or industrial scale procedures and include also those cases where different additions of appropriate precursors are made during the fermentation process in order to selectively increase the ratio of the single major components of a glycopeptidic antibiotic complex. See for instance U.K. Patent Application No. 8512795.

The pH value of the broth or the aqueous solution which is contacted with the polyamide resin may range between 4 and 10, preferably between 5 and 8. The solution to be contacted may contain variable amounts of water miscible solvents to prevent precipitation of solid materials which would plug the column.

The concentration of the antibiotic activity in the aqueous solution which is submitted to recovery operations according to this invention may vary within a wide range. Under the practical conditions currently applied in pilot and industrial scale operations, it is generally ranging from 50 to 20.000 p.p.m. (w/v).

When the potency of the starting broth is not too low, one single passage through the polyamide resin allows for reaching a satisfactory degree of purity.

The amount of polyamide resin employed for weight unit of antibiotic activity contained in the aqueous solution is in general depending on the absorption efficiency of the resin employed. Absorption efficiency of each resin may be determined through preliminary assays by successively adding several subdivided portions of a sample of an aqueous solution containing the glycopeptidic antibiotic in a certain concentration through a column packed with a certain volume of polyamide resin.

The portions of the eluate of the column are examined by HPLC to determine the glycopeptidic antibiotic content. When HPLC analysis reveals that the eluate of a certain portion of the test sample contains antibiotic activity, this is taken as an indication that the polyamide resin has been saturated and the amount of antibiotic adsorbed is calculated from the total volume of the eluate which did not show any antibiotic activity.

Preferably, the volume of polyamide employed in a pilot or industrial scale recovery process according to this invention is larger than the saturation volume which may be determined as described above.

In current operations, the ratio between the polyamide chromatography resin and glycopeptidic antibiotic activity to be recovered from an aqueous solution is usually ranging between about 50 and about 250, preferably between about 60 and about 200 liters of resin for kilogram of antibiotic activity contained in the solution.

The polyamide resin elution is generally carried out at room temperature by gravity or under suction or pressure by using as the eluent an aqueous solvent mixture, preferably, a solvent mixture of water and one or more water mixable organic solvents, e.g., a lower alkanol, acetone, methylethyl ketone, tetrahydrofuran, dioxane and acetonitrile.

The most preferred eluent mixtures are aqueous solution containing water and a lower alkanol (e.g. methanol) or acetone, in a proportion ranging from about 1:9 to about 9:1 (v/v), additioned with a suitable amount of an acid or a base soluble into said mixture to maintain the pH value of the eluate in the range between 3 and 11. Buffering solutions may also be employed to keep the pH value at the desired level.

Useful additions for said purpose are, for instance, mineral acids, formic acid, acetic acid, diluted aqueous alkali metal hydroxides such as sodium hydroxide, potassium hydroxide, sodium bicarbonate, sodium carbonate, ammonia, bis(2-hydroxyethylamine), sodium hydrogen phosphates buffers, and the like.

According to a preferred embodiment of the invention the first portion of the eluent mixture may have a pH value lower than the last portions and the pH value is gradually increased during the elution, thus allowing elimination of the more acidic impurities with the first fractions of the eluate. In said case, the first eluent portion may contain, for instance, aqueous sodium bicarbonate as the base, while the intermediate portions may contain sodium carbonate and the last portions may contain sodium hydroxide. Alternatively, after the elimination of the more acidic impurities, the elution of the antibiotic may be accomplished at an acidic pH value by using one of the above mentioned acids. Similar effects may also be obtained by using gradients of a gradient of water mixable solvents or increasing concentrations of buffering salts.

The eluates are collected in several fractions which are neutralized to pH 7 and analyzed by HPLC. The fractions containing glycopeptidic antibiotic activity are combined and concentrated under vacuum. The glycopeptidic antibiotic is recovered from said concentrated aqueous solution by common procedures. For instance, it may be precipitated from the concentrated aqueous solution by addition of water mixable organic solvent wherein the glycopeptidic has low solubility, e.g. acetone. An alternative recovery procedure which does not require addition of water mixable solvents is based on filtering the precipitated antibiotic at a pH near its isoelectric point from the concentrated solution after standing for a few hours at low temperature, e.g. 5° C.

In some instances, particularly in those cases wherein eluates contain an undesired amount of inorganic salts which make the product recovered by concentration not suitable for its direct use in the pharmaceutical practice, it is preferable to couple any further concentration of the eluate with a desalination procedure. Said operation may be simultaneously carried out by applying ultrafiltration techniques (for instance, by using membranes of the FILMTEC CO. having a cut-off of 500–1000 Dalton) or by pouring the eluate through a non-ionogenic macroreticular cross-linked resin (for instance, Amberlite XAD-7 or other resins of the type described in U.S. Pat. No. 3,531,463, U.S. Pat. No. 3,663,467 and UK No. 1581671) whereby the glicopeptide antibiotic is adsorbed from the aqueous mixture and then eluted with acetone/water mixture.

The glycopeptidic antibiotics recovered according to the above procedure possess a very satisfactory degree of purity in comparison with that obtainable by using different recovery procedures so far known or by using resins of different type such as, for instance, macroporous resins. The yields of recovery from the filtered fermentation broth or process streams according to the method of this invention are also very favorably comparable with those obtainable through the above mentioned prior-art procedures.

For instance, when the method of this invention is applied to teicoplanin, the antibiotic product from the column may already show a purity degree very close to the standard set up for its use in the pharmaceutical practice. In practical terms, for use in a pharmaceutical injectable dosage form such product requires only to be submitted to a further treatment for the elimination of pyrogenic substances such as, for instance, treating its solution in water or water/mixable organic solvents with activated charcoal.

The polyamide resins, once used for the recovery of a glycopeptidic antibiotic, can be utilized in many successive absorption-desorption cycles. Before reusing the polyamide resin, water washings are usually performed with at least 5 bed volumes of demineralized water. After three or four complete cycles, it is preferred to wash the resin with diluted caustic (pH 12) until the pH 12 is constant and then to wash again the resin with demineralized water until neutrality.

The following examples will make more understandable the invention without having any limiting purpose.

EXAMPLES

All the HPLC controls are carried out by using a Hewlett Packard apparatus Mo. 1084 equipped with a UV (254 m$\mu$) detector and a reverse phase C 18 prepacked column (Erbasil 5, 250×4 mm).

The mobile phases are: (A) 0,02M aqueous $NaH_2PO_4$/$CH_3CN$ 95:5 (v/v), (B) 0.02M aqueous $NaH_2PO_4$/$CH_3CN$ 25:75 (v/v). The gradient elution was from 8% of B to 55% of B in 40 minutes. Flow rate 1.5 ml/min.

EXAMPLE 1

170 liters of teicoplanin fermented broth made free from the mycelial cake were passed at pH 8, in 10 hours, through a 15×100 cm glass column filled with 10.5 liters of polyamide resin (Polyamide-CC 6 for column chromatography, particle size 50–160μ, apparent density 0.20 g/ml, Macherey Nagel, W. Germany) and kept under vacuum with suction from the bottom. The average flow rate was 100 ml/cm² h.

The exhausted broths (170 l) contained less than 5% of the starting teicoplanin activity and more than 80% of all the more polar components of the broth (unwanted solids and colored organic materials). After washing with 50 l of demineralized water, the resin elution was carried out with 50 l of a mixture of 9/1 methanol/water (v/v) containing a gradient from 0.3 to 1.0 g/l of sodium carbonate.

The eluates were collected in five fractions of ten liters each. Each fraction was neutralized to pH 7 with aqueous mineral acid and analyzed by HPLC analysis. Only two fractions (20 l) of the eluate were combined and the resulting solution (containing more than 90% of the eluted activity) was concentrated under reduced pressure at 45°–50° C. to 3.3 liters of aqueous residual suspension.

13.2 liters of acetone were added to the above concentrated teicoplanin suspension under stirring.

The precipitate was left to stand for 3 hours at room temperature and the clear surnatant acetone was decanted.

The solid was separated by filtration and the cake sludged with acetone at room temperature.

The product was filtered again and dried overnight under vacuum at room temperature.

Teicoplanin 85.7% pure by HPLC was obtained with a recovery yield of 81.9% on the starting microbiological activity contained in the fermented broth (water and solvent content: 11.5%, by weight; inorganic residue: 2.8%, by weight).

The 16.5 l mother liquors contained about 2% of the starting teicoplanin.

The absorption efficiency of the resin was preliminarily determined by the following procedure.

360 milliliters of a concentrated solution containing 3.1 g/l of crude teicoplanin was added in 50 ml portions to a column packed with 15 g (60 ml) of wet Polyamide-CC 6 resin. Every 50 ml portion of eluate was analyzed by HPLC to determine the teicoplanin content. 250 ml of solution were passed through the column and no teicoplanin was observed in the eluted solvent. The subsequent portion contained about 0.7 g/ml of activity. This was taken to indicate that 15 g of resin had been saturated by 0.9 g of teicoplanin. This value corresponds to 67 liter of Polyamide-CC 6 resin per kilogram of teicoplanin.

EXAMPLE 2

The following experiments were carried out on filtered fermentation broths obtained by adding to the fermentation medium appropriate precursors of the single components of teicoplanin factor $A_2$ according to U.K. Patent Application No. 8512795.

Polyamide-CC 6 resin of the same type of that employed in Example 1 was utilized as the adsorbent matrix. 60 l of fermented broth made free from the mycelial cake were passed onto a column containing 84 liter of resin per kilogram of activity. After washing with demineralized water the activity was eluted and precipitated following the procedure reported in example 1. Teicoplanin 86% HPLC pure was recovered with a 77% yield (water and solvent content 9.1%; inorganic residue 4.7%).

EXAMPLE 3

300 l of filtered fermentation broths obtained by adding L-valine to the fermentation medium according to U.K Patent Application No. 8512795 were passed at pH 6 through a 19×100 cm glass column containing 25 l Polyammide-SC 6 (particle size and other characteristics as described above). The exhausted broth did not contain any teicoplanin. After washing the column with 50 liter of demineralized water, the resin was washed with 50 l of aqueous solution of sodium acetate 0.05M (pH 8). More than 90% of the solid impurities present in the starting broth resulted to be eliminated. Then the antibiotics was eluted with 50 l of a mixture acetone/water 40:60 adjusted at pH 4 with acetic acid. The useful fractions cont ining 85% of the starting antibiotic were pooled together (30 liters). By concentration under reduced pressure at pH 6.5–7 the volume of the solution was reduced to about 12 l. By adding aqueous hydrochloric acid the pH was lowered again to 3.5–4 and the precipitated white solid was collected after standing 3 hours at +5° C. The cake was washed with acetone and filtered again. After drying teicoplanin was obtained with a 74% recovery yield and showed an HPLC purity of 83% (water and solvent content 14.1%, inorganic residue 2.1%).

EXAMPLE 4

450 g of crude deglucoteicoplanin obtained according to one of the examples reported in E.P.A. Publ. No. 146053 was dissolved in 7 l water at pH 8 and the solution was passed through a glass column (17×100 cm) containing 26 l Polyamide-PA 400 (M. Woelm). See the above description for particle size and other characteristics. After washing with 50 l of demineralized water the column was eluted with 250 l of a mixture methanol/water 9:1 containing 0.035 % w/v $Na_2CO_3$.

The useful fractions (100 l) were pooled and contained 85% of the loaded deglucoteicoplanin. The solution was then concentrated under reduced pressure at pH 6.5 until a residual volume of 9 l. After cooling the suspension was filtered and the cake washed with acetone. After drying, 83% HPLC pure deglucoteicoplanin (211 g; water and solvent content 12.2%) was obtained with a 79% yield (on the starting HPLC activity).

EXAMPLE 5

96 g of crude antibiotic L 17046 obtained as described in E.P.A. Publ.No. 119574 (HPLC assay 68%) is dissolved in 1 l of a mixture water/methanol 95:5 (v/v) at pH 8.2 and the solution is passed through a glass column (10×100 cm) containing 5 l of polyamide-SC 6. After washing with 5 l demineralized water, the column was washed with 5 l of a mixture of water/methanol 1:1 (v/v). The elution was carried out with a mixture methanol/water 9:1 (v/v) containing 0.03% (w/v) $Na_2CO_3$. The useful fractions containing 53.9 g of L 17046 (83% of the starting HPLC activity) were pooled together. By following the same procedure described in Example 4, 55.5 g of 89% HPLC pure L 17046 was obtained (water content 11%).

EXAMPLE 6

A fermented broth containing antibiotic A 40926 complex obtained as described in E.P.A. Ser. No.

85112406.5, made free from the mycelial mass by filtration at pH between 8.5 and 10.5 was acidified at pH 3 with sulfuric acid.

The precipitated crude material was collected by filtration and then dissolved in water at pH 7 and fed into a glass column containing Polyamide-SC 6AC of Macherey-Nagel & Co. (120 liters of resin per kilogram of antibiotic activity). After washing with demineralized water, a washing with 0.2M phosphate buffer at pH 8 was made to remove additional colored material. Alternatively, small amounts of detergents (e.g. sodium lauryl sulphate) can be added to water for the same purpose. The column content was then eluted with 1% aqueous ammonia obtaining about 75% of the starting antibiotic activity. The aqueous solution was brought to pH 3.5 by addition of 10% (w/v) aqueous HCl. and then cooled at 5° C. for a few hours. The precipitated product was separated by filtration, thoroughly washed with ice cooled water and then dried yielding HPLC substantially pure A 40926 antibiotic complex.

In a further experiment where the fermented filtered broth was directly fed to the column, after pH adjustment at 7, a 70% pure (HPLC) A 40926 was obtained. A second passage on Polyamide-SC 6AC or an adsorption/desorption cycle on affinity resin yielded HPLC pure material.

EXAMPLE 7

13.5 g of crude antibiotic $N^{63}$-[3-(dimethylamino)-propyl)] teicoplanin $A_2$ amide acetate obtained as described in example No. 1 of European Patent Application No. 86112226.5 is dissolved in 600 ml water at pH 6.5 and the solution is passed thorugh a glass column containing 250 g of polyamide SC 6 (0.1–0.3 mm). After washing with 500 ml water at pH 6.5, the elution was performed with a mixture of methanol/water 3:7 (v/v) at the same pH.

The useful fractions (ca 1.500 ml) were pooled and contained ca. 75% of the loaded antibiotic. After distilling off the methanol under vacuum the pH of the residual water solution was brought to 8.5 and the precipitated solid was collected after cooling, washed with water and dried u.v. 5.8 g of 85% HPLC pure $N^{63}$-[3-(dimethylamino)propyl)-]teicoplanin was obtained with an overall yield of 70%.

We claim:

1. A process for recovering a glycopeptidic antibiotic selected from teicoplanin and antibiotic A-40926 from aqueous solutions resulting from fermentation broths directly after filtering the mycelia which comprises contacting said aqueous solution with a polyamide column chromatography resin capable of absorbing said antibiotic activity, separating the resin from the aqueous solution, washing the resin with a aqueous mixture eluent and recovering the glycopeptidic antibiotic from said eluent.

2. A process as in claim 1 wherein the column chromatography polyamide resin is selected from polycaprolactame, nylon 6/6, nylon 6/9, nylon 6/10, nylon 6/12 and cross-linked polyvinylpyrrolidone.

3. A process as in claim 2 wherein the column chromatography polyamide resin is characterized by a pore volume (determined by means of mercury porosimeter) ranging between 1 and 5 ml/g, a surface area (determined by means of a mercury porosimeter) ranging between 1 and 100 m²/g, apparent density ranging between 0.15 and 0.50 g/ml, average pore diameter (determined by means of a mercury porosimeter) ranging between 100 and 3000 Angstrom units and particles size distribution where at least 40 percent of the particles have size lower than 300 μ.

4. A process as in claim 1 wherein the resin is selected from Polyamide-CC 6, Polyamide-SC 6, Polyamide-CC 6.6, Polyamide-CC 6AC, Polyamide-SC 6AC, Polyvinylpyrrolidone PVP-Cl, Polyamide PA 400.

5. A process as in claim 1 wherein the pH of the filtered fermentation ranges between 4 and 10.

6. A process as in claim 3 wherein the pH of the filtered fermentation ranges between 5 and 8.

7. A process as in claim 1 wherein the ratio between the polyamide chromatography resin and the glycopeptidic antibiotic activity is ranging between about 50 and about 250 liters of resin for kilogram of antibiotic activity contained in the solution.

8. A process as in claim 3 where the ratio between the polyamide chromatography resin and the glycopeptidic antibiotic activity is ranging between about 60 and about 200 liters of resin for kilogram of antibiotic activity contained in the solution.

9. A process as in claim 3 wherein the elution from the polyamide column chromatography resin is carried out by using as the eluent an aqueous solvent mixture.

10. A process according to claim 9 wherein said aqueous solvent mixture contains water and at least one organic solvent selected from the group consisting of a lower alkanol, acetone, methylethyl ketone, tetrahydrofuran, dioxane, and acetonitrile.

11. A process according to claim 10 in which the ratio of water to lower alkanol in said aqueous solvent mixture ranges from 1:9 to 9:1 (v/v).

* * * * *